(12) United States Patent
Saintigny et al.

(10) Patent No.: US 10,837,058 B2
(45) Date of Patent: Nov. 17, 2020

(54) MARKERS OF PAPILLARY AND RETICULAR FIBROBLASTS AND USES THEREOF

(71) Applicants: CHANEL PARFUMS BEAUTE, Neuilly sur Seine (FR); LEIDEN UNIVERSITY MEDICAL CENTER, Leiden (NL)

(72) Inventors: Gaelle Saintigny, Pantin (FR); Abdelouahab Elghalbzouri, Leiden (NL)

(73) Assignees: CHANEL PARFUMS BEAUTE, Neuilly sur Seine (FR); LEIDEN UNIVERSITY MEDICAL CENTER, Leiden (NL)

( * ) Notice: Subject to any disclaimer, the term of this patent is extended or adjusted under 35 U.S.C. 154(b) by 218 days.

(21) Appl. No.: 14/359,385

(22) PCT Filed: Nov. 23, 2012

(86) PCT No.: PCT/EP2012/073458
§ 371 (c)(1),
(2) Date: May 20, 2014

(87) PCT Pub. No.: WO2013/076240
PCT Pub. Date: May 30, 2013

(65) Prior Publication Data
US 2014/0323345 A1    Oct. 30, 2014

(30) Foreign Application Priority Data
Nov. 25, 2011    (EP) .................................... 11306566

(51) Int. Cl.
*C12Q 1/6876* (2018.01)
*G01N 33/50* (2006.01)
*G01N 33/569* (2006.01)

(52) U.S. Cl.
CPC ....... *C12Q 1/6876* (2013.01); *G01N 33/5023* (2013.01); *G01N 33/5044* (2013.01); *G01N 33/56966* (2013.01); *G01N 2333/4728* (2013.01); *G01N 2800/7042* (2013.01)

(58) Field of Classification Search
None
See application file for complete search history.

(56) References Cited

U.S. PATENT DOCUMENTS

| | | | |
|---|---|---|---|
| 7,192,719 B2 | 3/2007 | Asselineau et al. | |
| 2003/0152647 A1* | 8/2003 | Liu | A61K 36/185 424/725 |
| 2004/0142335 A1* | 7/2004 | Petersohn et al. | 435/6 |
| 2010/0291250 A1* | 11/2010 | Paufique | A61K 36/8905 424/779 |
| 2012/0283112 A1* | 11/2012 | Binder | G06F 19/18 506/8 |

FOREIGN PATENT DOCUMENTS

| | | |
|---|---|---|
| DE | 100 50 274 A1 | 4/2002 |
| WO | 02/053773 A2 | 7/2002 |

OTHER PUBLICATIONS

Brendel et al. (2005) Distinct Gene Expression Profile of Human Mesenchymal Stem Cells in Comparison to Skin Fibroblasts Employing cDNA Microarray Analysis of 9600 Genes. Gene Expression, 12:245-257.*
Mendez et al. (2009) A Genetic Expression Profile Associated with Oral Cancer Identifies a Group of Patients at High Risk of Poor Survival. Clinical Cancer Research, 15(4):1353-1361.*
Wicki et al. (2006) Tumor invasion in the absence of epithelial-mesenchymal transition: Podoplanin-mediated remodeling of the actin cytoskeleton. Cancer Cell, 9(4):261-272.*
Hunt et al. (2010) Botanical Extracts as Anti-Aging Preparations for the Skin: A Systematic Review. Drugs Aging, 27(12):973-985.*
Mine et al. (2008) Aging Alters Functionally Human Dermal Papillary Fibroblasts but Not Reticular Fibroblasts: A New View of Skin Morphogenesis and Aging. PLoS One, 3(12):e4066, pp. 1-13.*
Janson et al. (2012) Different Gene Expression Patterns in Human Papillary and Reticular Fibroblasts. Journal of Investigative Dermatology, 132:2565-2572.*
Michiels et al. (2005) Prediction of cancer outcome with microarrays: a multiple random validation strategy. Lancet, 365:488-492.*
Durchdewald et al. (2008) Podoplanin Is a Novel Fos Target Gene in Skin Carcinogenesis. Cancer Research, 68(17):6877-6883, and supplementary data.*
Buck et al. (1999) Design Strategies and Performance of Custom DNA Sequencing Primers. Biotechniques, 27(3): 528-536.*
Rozen et al. (2000) Primer3 on the WWW for general users and for biologist programmers. In: Krawetz S, Misener S (eds) Bioinformatics Methods and Protocols: Methods in Molecular Biology. Humana Press, Totowa, NJ, pp. 365-389.*

(Continued)

*Primary Examiner* — Neil P Hammell
(74) *Attorney, Agent, or Firm* — Nixon & Vanderhye

(57) ABSTRACT

An in vitro method for screening for candidate compounds for preventing and/or attenuating skin ageing, and/or hydrating skin, includes: a) contacting a test compound with a sample of papillary fibroblasts; b) measuring the expression of a gene selected from PDPN, CCRL1 and NTN1, in the papillary fibroblasts; and c) selecting compounds for which an activation of at least 1.5 fold of the expression of at least one of the genes is measured in the treated papillary fibroblasts compared with untreated papillary fibroblasts. Another in vitro method includes: a) contacting a test compound with a sample of reticular fibroblasts; b) measuring the expression of a gene selected from MGP, PPP1R14A and TGM2, in the reticular fibroblasts; and c) selecting compounds for which an activation of at most 1.0 fold of the expression of at least one of the genes is measured in the treated reticular fibroblasts compared with untreated reticular fibroblasts.

1 Claim, 2 Drawing Sheets
Specification includes a Sequence Listing.

(56) References Cited

OTHER PUBLICATIONS

Affymetrix HG-U133A 2.0 Annotation File (Accessed from: <http://www.affymetrix.com/estore/support/file_download.affx?onloadforward=/a nalysis/downloads/na35/ivt/HG-U133A_2.na35.annot.csv.zip&_reques☐ d=1267754#> on Aug. 1, 2016, filtered excerpt, 1 page.*
NM_006474.4 (*Homo sapiens* podoplanin (PDPN), transcript variant 1, mRNA, NCBI Reference Sequence, priority to Aug. 14, 2011).*
Kato et al. (2008) Molecular analysis of the pathophysiological binding of the platelet aggregation-inducing factor podoplanin to the C-type lectin-like receptor CLEC-2. Cancer Science, 99(1):54-61 (Year: 2008).*
Quatresooz Pascale et al.:"Immunohistochemical clues at aging of the skin microvascular unit", Journal of Cutaneous Pathology, vol. 36, No. I, Jan. 2009 (Jan. 2009), pp. 39-43, XP002675625, ISSN: 1600-0560 the whole document.
Mine Solene et al.: "Aging alters functionally human dermal papillary fibroblasts but not reticular fibroblasts: a new view of skin morphogenesis and aging.", PLOS One, vol. 3, No. 12, E4066, Dec. 2008 (Dec. 2008), pp. 1-13, XP002675626, ISSN: 1932-6203 the whole document.
International Search Report, dated Apr. 23, 2013, from corresponding PCT application.

* cited by examiner

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tgagggtcct acagagccaa cca                                            23

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ctcccccttc ccccaaccca                                                20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ttcaccgcat ccgtcgcctg                                                20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gagcgggtcc tgccttccct                                                20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gccatcctgg ccgccttagc                                                20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ttggtccctc ggcgcttcct                                                20

<210> SEQ ID NO 7
<211> LENGTH: 20
<212> TYPE: DNA
<213> ORGANISM: Artificial Sequence

```
<220> FEATURE:
<223> OTHER INFORMATION: primer

<400> SEQUENCE: 7
ccaacgagtg cgtggcctgt                                              20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ccggtgggtg atgggcttgc                                              20

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
gccaccagtc actccacgga gaa                                          23

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttggcagcag ggcgtaaccc                                              20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gctgcagtct ccatcgcggg                                              20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ggctgcctgt ggaggccttg                                              20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cgtgcagcgg ggcatcatca                                              20
```

-continued

```
<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tgcccagggc tcatcagggg                                               20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cacgaaccac ggcactgatt                                               20

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ttttcttgct gccagtctgg ac                                            22

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ggtgtccctg cagaacccgc                                               20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
cggggtctgg gatctccacc g                                             21
```

MARKERS OF PAPILLARY AND RETICULAR FIBROBLASTS AND USES THEREOF

FIELD OF THE INVENTION

The invention relates to the identification and the use of compounds which activate the expression of at least one gene selected from PDPN, CCRL1 and NTN1, for preventing and/or attenuating ageing, particularly photo-ageing, and/or for hydrating skin. The invention also relates to compounds that do not affect or inhibit the expression of at least one gene selected from MGP, PPP1R14A and TGM2, for preventing and/or attenuating ageing, particularly photo-ageing, and/or for hydrating skin.

BACKGROUND OF THE INVENTION

Skin performs important functions in life cycle; among them, it is an anatomical barrier against pathogens and damages (protection function). As skin ages, it becomes thinner and more easily damaged. A decrease in volume and elasticity is also observed during aging.

Photoaging corresponds to an accelerated aging of skin, due to intensive and/or frequent sun exposure.

In view of the biological evolution of skin during aging, there is an obvious need for active agents able to inhibit and/or reduce the effects of skin aging.

Particularly, there is a need for finding relevant markers of skin aging.

Skin is divided into two main compartments: epidermis and dermis. Dermis is a deeper layer than epidermis, and comprises fibroblasts, which synthetize collagen. It may be divided into papillary dermis and reticular dermis.

The superficial portion of papillary dermis is arranged into ridge-like structures, the dermal papillae, which contain microvascular and neural components that sustain the epidermis.

Reticular dermis extends from a superficial vascular plexus to a deeper vascular plexus, which serves as the boundary between the dermis and the hypodermis, which is rich in adipocytes.

It has been speculated that the papillary layer of the skin becomes thinner during skin aging. Both layers of papillary and reticular dermis comprise fibroblasts, but these cells have different properties and particularly express different markers.

Among these markers, CCRL1 is a C—C motif chemokine receptor, and its expression has been found in skin but its role in unknown. Netrin-1 (NTN1) is mainly known for its role in neuronal development. It can, depending on the context, attract or repel developing axons. Netrin-1 is expressed in skin, but its role is not known. Podoplanin (PDPN) is expressed in the skin, and is mainly known as a membrane protein in lymph vessels, but has also been shown to effect keratinocytes. Matrix Gla Protein (MGP) is an extracellular matrix protein mainly found in bone, but also in skin. PPP1R14A is best known as a myosin phosphatase inhibitor and as a regulator of smooth muscle contraction. Finally, transglutaminases are best known for their role in coeliac disease. One important process in which Transglutaminases 1, 3 and 5 are known to be involved is epidermal differentiation. TGM2s function in the epidermis is thought to be attaching the basal keratinocytes to the basal membrane.

Surprisingly, the inventors reached to identify specific markers of papillary and reticular dermis; said markers may be useful for identifying active agents against skin aging, but also for identifying papillary and reticular dermis.

When papillary fibroblasts are cultured for long periods, they become senescent and obtain a reticular signature. The inventors surprisingly demonstrate with the MGP marker that indeed the papillary layer is thinner in older donors compared to young donors.

Moreover, the inventors also showed that papillary fibroblasts differentiate into reticular fibroblasts with ageing, and that papillary fibroblasts increase epidermal longevity.

Therefore, the above mentioned active agents may prevent, reduce or even inhibit the cellular senescence, particularly the fibroblasts senescence, more particularly UV-induced cell senescence.

SUMMARY OF THE INVENTION

The present invention thus relates to an in vitro method for screening for candidate compounds for preventing and/or attenuating ageing of the skin, and/or for hydrating the skin, comprising the following steps:

a. bringing at least one test compound in contact with a sample of papillary fibroblasts;
b. measuring the expression of at least one gene selected from PDPN, CCRL1 and NTN1, in said papillary fibroblasts;
c. selecting the compounds for which an activation of at least 1.5 fold of the expression of at least one of said genes is measured in the papillary fibroblasts treated in a. compared with the untreated papillary fibroblasts.

The present invention also relates to an in vitro method for screening for candidate compounds for preventing and/or attenuating ageing of the skin, and/or for hydrating the skin, comprising the following steps:

a. bringing at least one test compound in contact with a sample of reticular fibroblasts;
b. measuring the expression of at least one gene selected from MGP, PPP1R14A and TGM2, in said reticular fibroblasts;
c. selecting the compounds for which an activation of at most 1.0 fold of the expression of at least one of said genes is measured in the reticular fibroblasts treated in a. compared with the untreated reticular fibroblasts.

According to a first embodiment, step b. is performed before and after step a. In this case, the expression of at least one gene selected from PDPN, MGP, CCRL1, PPP1R14A, NTN1 and TGM2, measured in the fibroblasts (papillary or reticular) before step a. corresponds to the control value (i.e. untreated fibroblasts). Thus, on one hand, in the case of PDPN, CCRL1 and/or NTN1 markers, step c. comprises the selection of the compounds for which an activation of at least 1.5 fold of the expression of at least one gene selected from PDPN, CCRL1 and NTN1 is measured in the papillary fibroblasts treated in a. compared with the same papillary fibroblasts before step a. On the other hand, in the case of MGP, PPP1R14A and/or TGM2 markers, step c. comprises the selection of the compounds for which an activation of at most 1.0 fold of the expression of at least one gene selected from MGP, PPP1R14A and TGM2 is measured in the reticular fibroblasts treated in a. compared with the same reticular fibroblasts before step a.

According to another embodiment, the method comprises a first step a'. of preparing samples of fibroblasts, papillary or reticular. Thus, preferably, the present invention relates to an in vitro method for screening for candidate compounds for preventing and/or attenuating ageing of the skin, and/or for hydrating the skin, comprising the following steps:

a'. preparing at least two samples of papillary fibroblasts;
a. bringing one of the samples into contact with at least one test compound; then
b. measuring the expression of at least one gene selected from PDPN, CCRL1 and NTN1, in said samples; and
c. selecting the compounds for which an activation of at least 1.5 fold of the expression of at least one of said genes is measured in the papillary fibroblasts treated in a. as compared to the untreated papillary fibroblasts.

The present invention also relates to an in vitro method for screening for candidate compounds for preventing and/or attenuating ageing of the skin, and/or for hydrating the skin, comprising the following steps:
a'. preparing at least two samples of reticular fibroblasts;
a. bringing one of the samples into contact with at least one test compound; then
b. measuring the expression of at least one gene selected from MGP, PPP1R14A and TGM2, in said samples; and
c. selecting the compounds for which an activation of at most 1.0 fold of the expression of at least one of said genes is measured in the reticular fibroblasts treated in a. as compared to the untreated reticular fibroblasts.

In this second embodiment, the expression of at least one gene selected from PDPN, MGP, CCRL1, PPP1R14A, NTN1 and TGM2, measured in the sample of fibroblasts (papillary or reticular) not submitted to step a. corresponds to the control value (i.e. untreated fibroblasts).

DETAILED DESCRIPTION OF THE INVENTION

Figure 1:
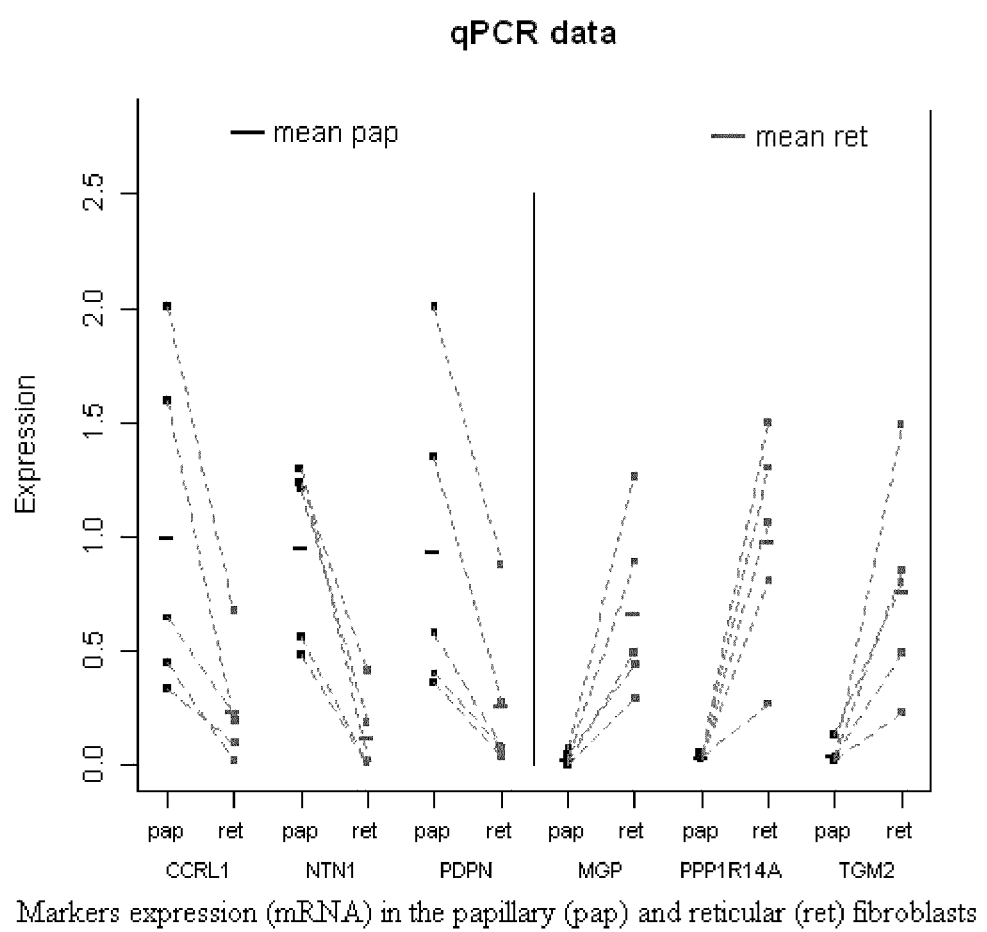
FIG. 1 shows the results of qPCR analysis of six marker genes in papillary and reticular fibroblasts.

By the expression "ageing of the skin" is intended any change in the external appearance of the skin due to ageing, preferably due to photo-induced ageing or photo-aging, such as, for example, wrinkles and fine lines, withered skin, flaccid skin, thinned skin, and skin lacking elasticity and/or tonus, and also any internal change in the skin which is not systematically reflected by a changed external appearance, such as, for example, any internal degradation of the skin, particularly of collagen, following exposure to ultraviolet radiation.

By "hydrating the skin", it is meant maintaining the natural humidity of the skin and preventing its drying, notably by improving skin cell communication and function, including improving its barrier function.

The test compounds may be of any type. They may be of natural origin or may have been produced by chemical synthesis. This may involve a library of structurally defined chemical compounds, uncharacterized compounds or substances, or a mixture of compounds.

Natural compounds include compounds from animal or vegetal origin, like plants. Preferably, the test compounds are vegetal, preferably chosen from botanical extracts.

The present invention also relates to an in vitro method for detecting the presence of papillary fibroblasts and of reticular fibroblasts in a biological sample, comprising the step of measuring the expression of at least one gene selected in the group consisting of PDPN, MGP, CCRL1, PPP1R14A, NTN1 and TGM2 in said fibroblasts. If PDPN, CCRL1 and/or NTN1 genes are significantly expressed, then papillary fibroblasts are detected. If MGP, PPP1R14A and/or TGM2 genes are significantly expressed, then reticular fibroblasts are detected.

The present invention also relates to an in vitro method for monitoring the differentiation of papillary fibroblasts into reticular fibroblasts in a biological sample, comprising the step of measuring the expression of at least one gene selected in the group consisting of PDPN, MGP, CCRL1, PPP1R14A, NTN1 and TGM2 in said fibroblasts. If PDPN, CCRL1 and/or NTN1 genes are significantly expressed, then papillary fibroblasts are the main population and few or no differentiation occurs. If MGP, PPP1R14A and/or TGM2 genes are significantly expressed, then reticular fibroblasts are the main population and differentiation occurs.

According to step a. of the method according to the invention, the test compound is put into contact with a sample of fibroblasts.

According to step b., the expression of at least one gene selected from PDPN, MGP, CCRL1, PPP1R14A, NTN1 and TGM2 is measured in said fibroblasts.

The term "expression of at least one gene selected from PDPN, MGP, CCRL1, PPP1R14A, NTN1 and TGM2" is intended to mean the mRNA of the corresponding gene, or the protein encoded by the corresponding gene. Said gene expression may thus be measured by quantifying the mRNA or the protein. This is notably shown in examples 1 or 2.

Those skilled in the art are familiar with the techniques for quantitatively or semi-quantitatively detecting the mRNA of the gene of interest, and thus, determining said gene expression. Techniques based on hybridization of the mRNA with specific nucleotide probes are the most common, like Western or Northern blotting, RT-PCR (reverse transcriptase polymerase chain reaction), quantitative RT-PCR (qRT-PCR).

The expression of at least one gene selected from PDPN, MGP, CCRL1, PPP1R14A, NTN1 and TGM2 after treatment with the test compound is then compared to a control value, i.e. a value obtained in the same fibroblasts before treatment, or a value obtained in another sample of fibroblasts which are untreated.

According to step c., the useful compounds are those for which an activation of at most 1.0 fold of the expression of at least one gene MGP, PPP1R14A or TGM2, or an activation of at least 1.5 fold of the expression of at least one gene PDPN, CCRL1 or NTN1, is measured in the fibroblasts (respectively reticular or papillary) treated in a. as compared to the untreated fibroblasts (respectively reticular or papillary).

The compounds selected by means of the screening methods defined herein can subsequently be tested on other in vitro and/or ex vivo models and/or in vivo models (in animals or humans) for their effects on skin ageing and/or skin hydration. The useful compounds according to the invention are activators of the targeted PDPN, CCRL1 and/or NTN1 genes, and/or inhibitors of MGP, PPP1R14A and/or TGM2 genes.

A subject of the invention is also the cosmetic use of an activator of the expression of at least one gene selected from PDPN, CCRL1 and NTN1, which can be obtained according to the above described method, for preventing and/or attenuating ageing of the skin and/or for hydrating the skin.

According to another aspect, an object of the present invention is the use of at least one activator of the expression of at least one gene selected from PDPN, CCRL1 and NTN1, which can be obtained according to the above described method, to make a therapeutic composition for preventing and/or attenuating ageing of the skin and/or for hydrating the skin. The present invention thus also relates to the use of at least one activator of the expression of at least one gene selected from PDPN, CCRL1 and NTN1, which can be obtained according to the above described method, for preventing and/or attenuating ageing of the skin and/or for hydrating the skin.

The activator refers to a compound which substantially increases the expression of at least one gene selected from PDPN, CCRL1 and NTN1, i.e. the quantity of at least one mRNA or protein encoded by at least one of the corresponding genes. The term "substantially" means an increase of at least 1.5 fold, preferably of at least 2 fold.

The activator can be used in a proportion of from 0.0001 to 10% by weight, preferably in a proportion of from 0.01 to 5% by weight of the composition.

A subject of the invention is also the cosmetic use of an inhibitor of the expression of at least one gene selected from MGP, PPP1R14A and TGM2, which can be obtained according to the above described method, for preventing and/or attenuating ageing of the skin and/or for hydrating the skin.

According to another aspect, an object of the present invention is the use of at least one inhibitor of the expression of at least one gene selected from MGP, PPP1R14A and TGM2, which can be obtained according to the above described method, to make a therapeutic composition for preventing and/or attenuating ageing of the skin and/or for hydrating the skin. The present invention thus also relates to the use of at least one inhibitor of the expression of at least one gene selected from MGP, PPP1R14A and TGM2, which can be obtained according to the above described method, for preventing and/or attenuating ageing of the skin and/or for hydrating the skin.

The inhibitor refers to a compound which substantially decreases or does not change the expression of at least one gene selected from MGP, PPP1R14A and TGM2, i.e. the quantity of at least one mRNA or protein encoded by at least one of the corresponding genes.

The inhibitor can be used in a proportion of from 0.0001 to 10% by weight, preferably in a proportion of from 0.01 to 5% by weight of the composition.

The activator or inhibitor may be chosen from organic molecules, but may also be a botanical extract.

The activators and inhibitors identified thanks to the screening method described above can be formulated within a composition, in combination with a physiologically acceptable carrier, preferably a cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user. These compositions may be administered, for example, orally, or topically. Preferably, the composition is applied topically. By oral administration, the composition may be in the form of tablets, gel capsules, sugar-coated tablets, syrups, suspensions, solutions, powders, granules, emulsions, suspensions of microspheres or nanospheres or lipid or polymeric vesicles for controlled release. By topical administration, the composition is more particularly for use in treating the skin and may be in the form of salves, creams, milks, ointments, powders, impregnated pads, solutions, gels, sprays, lotions or suspensions. It may also be in the form of suspensions of microspheres or nanospheres or lipid or polymeric vesicles or polymeric patches or hydrogels for controlled release. This composition for topical application may be in anhydrous form, in aqueous form or in the form of an emulsion. The composition for topical application may be in the form of an oil-in-water, water-in-oil or multiple emulsion (W/O/W or O/W/O), which may optionally be microemulsions or nanoemulsions, or in the form of an aqueous dispersion, a solution, an aqueous gel or a powder. In a preferred variant, the composition is in the form of a gel, a cream or a lotion.

The physiologically acceptable carrier of the composition generally comprises water and optionally other solvents such as ethanol.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may comprise various adjuvants, such as at least one compound chosen from:
  oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;
  waxes such as ozokerite, polyethylene wax, beeswax or carnauba wax;
  silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogenopolysiloxane;
  surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;
  co-surfactants such as linear fatty alcohols and in particular cetyl alcohol and stearyl alcohol;
  thickeners and/or gelling agents, and in particular crosslinked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);
  organic screening agents, such as dibenzoylmethane derivatives (including butylmethoxydibenzoylmethane), cinnamic acid derivatives (including ethylhexyl methoxycinnamate), salicylates, para-aminobenzoic acids, β,β'-diphenyl acrylates, benzophenones, benzylidenecamphor derivatives, phenylbenzimidazoles, triazines, phenylbenzotriazoles and anthranilic derivatives;

inorganic screening agents, based on mineral oxides in the form of coated or uncoated pigments or nanopigments, and in particular based on titanium dioxide or zinc oxide;
dyes;
preserving agents;
sequestrants such as EDTA salts;
fragrances;
and mixtures thereof, without this list being limiting.

Examples of such adjuvants are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition may also comprise at least one compound with an optical effect such as fillers, pigments, nacres, tensioning agents and matting polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, silica, kaolin, nylon powders such as Nylon-12 (ORGASOL® sold by the company Atochem), polyethylene powders, polyurethane powders, polystyrene powders, polyester powders, optionally modified starch, silicone resin microbeads such as those sold by the company Toshiba under the name TOSPEARL®, hydroxyapatite, and hollow silica microspheres (silica beads from the company Maprecos).

The term "pigments" should be understood as meaning white or colored, mineral or organic particles that are insoluble in the medium, which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychoride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom.

Tensioning agents that may be mentioned include polymers of natural origin. The term "polymer of natural origin" means polymers of plant origin, polymers derived from integuments, egg proteins and latices of natural origin. These polymers are preferably hydrophilic. Polymers of plant origin that may especially be mentioned include proteins and protein hydrolyzates, and more particularly extracts of cereals, of legumes and of oil-yielding plants, such as extracts of corn, of rye, of wheat, of buckwheat, of sesame, of spelt, of pea, of bean, of lentil, of soybean and of lupin. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (AQUAMERE S-2001® from the company Hydromer).

The term "matting polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG by the company Shin-Etsu, under the name TREFIL®, BY29 or EPSX by the company Dow Corning or under the name GRANSIL® by the company Grant Industries.

The composition used according to the invention may also comprise active agents other than the activator or inhibitor, and in particular at least one active agent chosen from: agents that stimulate the production of growth factors; anti-glycation or deglycating agents; agents that increase collagen synthesis or that prevent its degradation (anti-collagenase agents and especially matrix metalloprotease inhibitors); agents that increase elastin synthesis or prevent its degradation (anti-elastase agents); agents that stimulate the synthesis of integrin or of focal adhesion constituents such as tensin; agents that increase the synthesis of glycosaminoglycans or proteoglycans or that prevent their degradation (anti-proteoglycanase agents); agents that increase fibroblast proliferation; depigmenting or anti-pigmenting agents; antioxidants or free-radical scavengers or anti-pollution agents; and mixtures thereof, without this list being limiting.

Examples of such agents are especially: plant extracts and in particular extracts of *Chondrus crispus*, of *Thermus thermophilus*, of *Pisum sativum* (PROTEASYL® TP LS), of *Centella asiatica*, of Scenedesmus, of *Moringa pterygosperma*, of witch hazel, of *Castanea sativa*, of *Hibiscus sabdriffa*, of *Polianthes tuberosa*, of *Argania spinosa*, of *Aloe vera*, of *Narcissus tarzetta*, or of liquorice; an essential oil of *Citrus aurantium* (Neroli); α-hydroxy acids such as glycolic acid, lactic acid and citric acid, and esters thereof; β-hydroxy acids such as salicylic acid and derivatives thereof; plant protein hydrolyzates (especially of soybean or of hazelnut); acylated oligopeptides (sold especially by the company Sederma under the trade names MAXILIP®, MATRIXYL® 3000, BIOPEPTIDE® CL or BIOPEPTIDE® EL); yeast extracts and in particular of *Saccharomyces cerevisiae*; algal extracts and in particular of laminairia; vitamins and derivatives thereof such as retinyl palmitate, ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate; arbutin; kojic acid; ellagic acid; and mixtures thereof.

As a variant or in addition, the composition used according to the invention may comprise at least one elastase inhibitor (anti-elastase), such as an extract of *Pisum sativum* seeds that is sold especially by the company Laboratoires Sérobiologiques/Cognis France under the trade name PROTEASYL TP LS®.

The composition may also contain inert additives or combinations of these additives, such as wetting agents, stabilizers, moisture regulators, pH regulators, osmotic pressure modifiers, or UV-A and UV-B screens.

The following examples illustrate the invention without limiting the scope thereof.

EXAMPLES

Example 1

Different Expression Patterns in Papillary and Reticular Fibroblasts

Material and Methods

Isolation and Cell Culture 5 female, Caucasian, donors aged 39-49 were used for the isolation of the fibroblasts. Of all donors both reticular and papillary were isolated, consequently all analyses were performed on a pair wise basis. Isolation was performed as described in the literature (12,13). In short, skin obtained from plastic surgery (mamma reduction or abdominal correction) was cleaned thoroughly and dermatomized at two different depths. First, a 300 µm piece was taken, containing the epidermis and papillary dermis. For the reticular dermis the skin was dermatomized at 700 µm, and the upper part was discarded. The remaining (deep) dermis was used for fibroblast isolation. Fibroblasts were isolated by treatment with Collagenase (Invitrogen, Breda, The Netherlands)/Dispase (Roche Diagnostics, Almere, The Netherlands) (3:1) for 2 hours at 37 C. The cells were subsequently filtered with a 70 µm cell strainer and cultured in DMEM medium (Invitrogen) containing 5% Fetal Calf Serum (FCS, HyClone/Greiner, Nürtingen, Germany) and 1% penicillin-streptomycin (Invitrogen). They were kept at 37° C. at 5% $CO_2$. Fibroblasts used for experiments were in passage 4-6.

For the growth curve experiment 5000 fibroblasts were seeded into 6-wells plates. Cells were counted with a Bürker counting chamber after 3, 6, 7 and 10 days.

RNA, Protein Isolation

RNA and proteins were isolated from monolayer fibroblast cultures with the RNEasy kit (Qiagen) and Mammalian Protein Extraction Reagent (M-PER, Thermo Scientific), respectively, according to the manufacturer's instructions. All following experiments were performed with RNA and proteins from a single isolation.

Microarrays

Gene expression analysis was performed by ServiceXS (Leiden, The Netherlands). The platform was Illumina HumanHT-12 Expression BeadChip. Data were generated with the Beadstudio software of Illumina and analysis was performed in R (2.10.0). For the analysis the data were imported and normalized with the lumi package (Robust Spline Normalization) (16) and followed by expression analysis with the limma package (17). Probes that showed no expression in all of the arrays (Detection P value>0.05) were not included in the analysis. For multiple testing correction the FDR method was used (18).

Pathway Analysis

Pathway- and GO term enrichment analysis was performed with the DAVID tool (19). Two lists were uploaded; one with genes that were upregulated in reticular fibroblasts (adj. p value<0.1 and LogFC>0.7) and one with genes upregulated in papillary fibroblasts (adj. p value<0.1 and LogFC<−0.7). Both lists had approximately 80 genes.

qPCR cDNA was generated of 1 µg RNA using the iScript cDNA synthesis kit (BioRad, Veenendaal, The Netherlands) according to manufacturer's instructions. PCR reactions were based on the SYBR Green method (BioRad) and consisted of 2× Sybr Green Mastermix, 1 ng cDNA template and 500 nM of forward and reverse primers. The PCRs were run on the MyIQ system (BioRad). The PCR cycles were: 3,5 minutes at 95 C to activate the polymerase, 35 cycles of 20 sec 95 C and 40 sec 60 C, followed by the generation of a melt curve. Primers were checked before on dilution series of normal fibroblasts cDNA. References genes were analyzed with the GeNorm method (20). Expression analysis was performed with the BioRad Software (iQ5) and was based on the delta delta Ct method with the reference genes that were most stably expressed in the GeNorm analysis.

The primers are listed in Table 1:

TABLE 1

Primers used for the experiment.

| Target | Sequence Forward | Sequence Reverse |
| --- | --- | --- |
| CCRL1 | TGAGGGTCCTACAGAGCCAACCA (SEQ ID NO: 1) | CTCCCCCTTCCCCCAACCCA (SEQ ID NO: 2) |
| EI24 | TTCACCGCATCCGTCGCCTG (SEQ ID NO: 3) | GAGCGGGTCCTGCCTTCCCT (SEQ ID NO: 4) |
| MGP | GCCATCCTGGCCGCCTTAGC (SEQ ID NO: 5) | TTGGTCCCTCGGCGCTTCCT (SEQ ID NO: 6) |
| NTN-1 | CCAACGAGTGCGTGGCCTGT (SEQ ID NO: 7) | CCGGTGGGTGATGGGCTTGC (SEQ ID NO: 8) |
| PDPN | GCCACCAGTCACTCCACGGAGAA (SEQ ID NO: 9) | TTGGCAGCAGGGCGTAACCC (SEQ ID NO: 10) |
| R14A | GCTGCAGTCTCCATCGCGGG (SEQ ID NO: 11) | GGCTGCCTGTGGAGGCCTTG (SEQ ID NO: 12) |
| SND1 | CGTGCAGCGGGGCATCATCA (SEQ ID NO: 13) | TGCCCAGGGCTCATCAGGGG (SEQ ID NO :14) |
| TBP | CACGAACCACGGCACTGATT (SEQ ID NO: 15) | TTTTCTTGCTGCCAGTCTGGAC (SEQ ID NO: 16) |
| TGM2 | GGTGTCCCTGCAGAACCCGC (SEQ ID NO: 17) | CGGGGTCTGGGATCTCCACCG (SEQ ID NO: 18) |

Underlined genes were reference genes.

Western Blot

7 µg of each protein sample were added to Loading Buffer, heated to 90° C. for 5 minutes and loaded on a 10% SDS-PAGE gel. After electrophoresis the proteins were blotted on a PVDF membrane (Thermo Scientific, Etten-Leur, The Netherlands). Blocking was performed with 5% Protifar Plus (Nutricia, The Netherlands) in PBS-T (0,1% Tween). Primary antibodies were incubated O/N at 4° C. (listed in Table 2). Afterwards, membranes were incubated with the appropriate secondary antibodies, either stabilized HRP conjugated anti-mouse or anti-rabbit (Thermo Scientific/Pierce, dilution 1:1500). For detection of the bands, the Supersignal West Femto ECL system (Thermo Scientific/Pierce) was applied to the membrane. Bands were visualized using G-box technology and software.

TABLE 2

Antibodies used in this study.

| Antibody | Dilution (WB/IHC) | Supplier |
|---|---|---|
| α-SMA (1A4) | NA/1:800 | Sigma |
| CCRL1 (ab74806) | 1:1000/1:1000 | Abcam |
| MGP (A-11) | 1:500/1:100 | Santa Cruz |
| NTN-1 (H-104) | 1:500/1:75 | Santa Cruz |
| PDPN (18H5) | 1:1000/1:100 | Abcam |
| TGM2 (CUB 7402) | 1:1000/1:100 | Abcam |
| Vimentin (V9) | NA/1:50 | Oncogene |

NA = Not Applicable

IHC

For IHC on monolayer cell cultures, fibroblasts were grown on glass slides until nearly confluent, washed in PBS and fixed with 4% formaldehyde. Primary antibodies are shown in Table 2. Staining was visualized by a secondary antibody with a fluorescent dye (Cy3). DAPI was used as counterstain.

Immunohistochemical analysis was performed on paraffin embedded in vivo skin sections. 5 µm thick slides were cut, deparaffinized, rehydrated and washed with PBS. Heat mediated antigen retrieval at PH 6 was performed, followed by a block of endogenous peroxidase and a block step using PBS/1% BSA/2% normal human serum. Primary antibodies were incubated overnight at 4° C. Staining was visualized using BrightVision+poly-HRP (Immunlogic, Duiven, The Netherlands) according to manufacturer's instructions, and DAB as a chromogen. Counterstaining was performed with haematoxylin.

Results

Distinct Morphology of Papillary and Reticular Fibroblasts

Cultured reticular and papillary fibroblasts revealed morphological characteristics as described in the literature (e.g. (1,12)). Papillary fibroblasts exhibit a spindle-shaped morphology, whereas reticular fibroblasts are characterized by a more flattened appearance with an increased expression of the myofibroblast marker alpha-smooth muscle actin (α-SMA). Additionally, papillary fibroblasts showed increased proliferation (data not shown).

Differentially Expressed Genes in Reticular and Papillary Fibroblasts

Gene expression analysis revealed 116 probes differentially expressed in reticular and papillary fibroblasts (adjusted p value<0.05) (data not shown).

In reticular fibroblasts, genes belonging to the smooth muscle contraction pathway were particularly overexpressed, confirming the fact that reticular populations contain more α-SMA positive fibroblasts. GO term analysis of our data showed that reticular fibroblasts contain predominantly genes involved in cytoskeletal organization, cell motility and neuronal development.

Papillary fibroblasts showed a high expression level of genes belonging to the complement activation pathway, indicating an implication of the immune response system. This was confirmed by investigating the GO terms which showed enrichment for immune response, host defense and complement activation.

Three reference genes were selected for the qPCR experiment following GeNorm analysis: SND1, TBP and EI24. 16 significantly different genes from the gene expression data were chosen to be validated by qPCR. 13 of these were also significantly different in the qPCR analysis (data not shown).

Validation of Markers on Protein Level

Of the genes that were confirmed by qPCR, six were selected for further validation at the protein level. These were CCRL1 (C—C chemokine receptor type 11), MGP (Matrix Gla Protein), NTN1 (Netrin-1), PDPN (Podoplanin), TGM2 (Transglutaminase 2), and PPP1R14A (Homo sapiens protein phosphatase 1, regulatory (inhibitor) subunit 14A) (see FIG. 1). The selection was based on a high LogFC and expression at the cell surface (except TGM2, which is expressed intracellularly). Two of these (TGM2 and PDPN) could be validated by Western Blot on cell lysates of the same donors used in the array experiment (data not shown). One of the targets, CCRL1, was not different at the protein level, based on Western Blot experiments.

TGM2 and PDPN were stained on monolayer cultures of reticular and papillary fibroblasts. PDPN showed strong staining in papillary fibroblasts and weak staining in reticular fibroblasts, whereas TGM2 was expressed in most, but not all, reticular fibroblasts and only occasionally in papillary fibroblasts (FIG. 1).

Immunohistochemical analyses were performed on in vivo paraffin sections of female donors. As expected from our gene expression data, MGP was more abundant in the reticular dermis (matrix) (data not shown). Donors of different ages showed a reduction with age of the papillary dermis based on analysis of the MGP negative band. Netrin-1 and PDPN were highly expressed in the papillary dermis, even though, not all papillary fibroblasts were positive and several reticular fibroblasts showed positive staining (data not shown). CCRL1 is not expressed in fibroblasts. TGM2 expression was only found sporadically and was highly variable between different donors.

Therefore, as a conclusion, it can be said that at least PDPN and NTN-1 are papillary markers, and that at least MGP and PPP1R14A are reticular markers.

Example 2

Papillary Fibroblasts Differentiate into Reticular Fibroblasts with Ageing

The most prominent characteristic of (intrinsically) aged skin is the disappearance of ridges/dermal papillae. With this loss of the ridges, also a part of the papillary dermis is lost. The hypothesis was thus that during skin aging a (relative) shift occurs from papillary to a predominantly reticular phenotype. This was proposed before by Mine et al. (Mine S, Fortunel N O, Pageon H, Asselineau D. Aging alters functionally human dermal papillary fibroblasts but not reticular fibroblasts: a new view of skin morphogenesis and aging. *PLoS ONE* 2008; 3: e4066.). Differentiation of fibroblasts, from papillary to reticular, could explain this shift during skin aging. Therefore it was investigated whether papillary fibroblasts change expression of the markers after prolonged in vitro culture.

Method

Papillary fibroblasts were maintained in culture for several weeks—months (and subcultured when reaching confluence). The expression of the reticular and papillary markers in 3 populations was compared: low passage papillary, high passage papillary (long cultured) and low passage reticular fibroblasts. The markers were measured by qPCR and immunohistochemistry on monolayers.

Fibroblast derived matrix (FDM) human skin equivalents (HSE) were generated. In this type of HSE, fibroblasts are seeded in wells and stimulated to produce extracellular matrix for 2-3 weeks. This is subsequently used to seed keratinocytes on and generate a full-thickness skin equivalent. These skin equivalents were analysed by Haematoxylin-Eosin (HE) staining and immunohistochemistry.

Results qPCR analysis revealed that compared to low passage papillary fibroblasts, high passage papillary fibroblasts have a decreased expression of papillary markers and an increased expression of reticular markers. This suggests that papillary fibroblasts differentiate into reticular fibroblasts after prolonged culture. Indeed, the papillary marker PDPN, present in low passage papillary fibroblasts, is absent after prolonged culture (high passage) of papillary fibroblasts and in reticular fibroblasts. The reticular marker TGM2 and myofibroblast marker a-SMA (alpha smooth muscle actin) are absent or very lowly expressed in low passage papillary fibroblasts, and are increased in high passage papillary and reticular fibroblasts.

Thus, after prolonged culture papillary fibroblasts lose expression of papillary markers and gain expression of reticular markers, as compared to low passage papillary controls (data not shown).

In HSE generated with papillary fibroblasts (HSE-PF) a looser extracellular matrix is formed, which seems to better support the epidermal growth (in terms of differentiation and proliferation) than HSEs generated with reticular fibroblasts (HSE-RF). After prolonged culture, HSE-PF behave more like HSE-RF than to low passage HSE-PF.

Indeed, high passage HSE-PF have a more similar morphology to HSE-RF than to low passage HSE-PF. Low passage HSE-PF generate a loose matrix, have a high keratinocyte density and a smooth looking epidermis. On the other hand, high passage HSE-PF and low passage HSE-RF have a dense matrix, low keratinocyte density and a rugged looking epidermis.

Example 3

TGF-β Induces Differentiation of Papillary into Reticular Fibroblasts

TGF-β1 can induce differentiation of fibroblasts to myofibroblasts. Myofibroblasts, in turn, share some characteristics with reticular fibroblasts, such as large cell bodies and high contractility. The myofibroblast marker aSMA (alpha smooth muscle actin) is expressed by all myofibroblasts, but only in a small fraction of reticular fibroblasts (1-5%). a-SMA is hardly present in papillary fibroblasts.

Method

Monolayer cultures of papillary fibroblasts were treated with TGF-β1, 2 or 10 ng/mL, for 2 or 4 days. Then the expression of the reticular and papillary markers was measured by qPCR and by IHC staining on the cultures.

Results

Addition of TGF-β1 to papillary fibroblasts caused differentiation to reticular fibroblasts in monolayer cell cultures, as measured by qPCR. The expression of papillary markers decreased and the expression of reticular markers increased (data not shown). The findings were validated by IHC staining, in which again a loss of papillary marker PDPN and a gain of reticular marker TGM2 was found. TGF-β1 also induced (some) myofibroblast differentiation, as seen by morphological changes (increase in cell size) and increased a-SMA expression. However, the increase in the "reticular marker-positive" cells (for TGM2) was higher than the increase in a-SMA positive cells.

Example 4

Papillary Fibroblasts Increase Epidermal Longevity

Method

Two functional characteristics of epidermal stem cells were used in these experiments:

adherence and longevity. Keratinocyte stem cells are believed to have a fast-adhering capacity. Therefore an experiment was performed, in which the keratinocytes were only allowed to attach for a very short period (ranging from 1 to 10 minutes). This enriches the population for potential stem cells. Then these populations were cultured in medium conditioned by papillary and reticular fibroblasts.

In another experiment secreted factors by papillary and reticular fibroblasts were investigated on epidermal stemness. Therefore, epidermal equivalents were generated and cultured for two weeks in conditioned medium of reticular and papillary fibroblasts. For the final experiment FDM HSE were generated with papillary and reticular fibroblasts (HSE-PF and HSE-RF). Two aspects were performed differently this time. First, the keratinocytes were seeded in a ring. The seeded keratinocytes then only attach in the centre and (should) migrate over the entire (fibroblast derived) matrix during the rest of the culture period. Second, the HSEs were cultured for longer than normal. Normally FDM equivalents are cultured for 14-17 days after air exposure, but now they were harvested after 3, 7 or 10 weeks of air exposure.

Results

HSEs were generated with papillary or reticular fibroblasts. Keratinocytes were seeded in a ring and left to attach, after which the ring was removed to allow keratinocyte migration over the matrix. HSEs were photographed before harvest and the area that the keratinocytes had covered was measured and calculated as a percentage of total matrix area. The keratinocytes migrated over a larger area on papillary matrices than on reticular matrices.

After 10 weeks there was hardly any viable epidermis left in HSE-RF, while in HSE-PF several layers of viable cells were still present. In HSE-RF the number of proliferating basal keratinocytes is decreased compared to HSE-PF. After 10 weeks keratinocyte proliferation in HSE-RF was strongly reduced, while in HSE-PF there were still ample proliferating keratinocytes (though it decreases as well compared to 3 and 7 weeks).

The results of the conditioned medium experiments can be summarized as follows: conditioned medium of reticular or papillary fibroblasts had no effect on the growth of keratinocytes, fastadhering keratinocytes or epidermal skin equivalents.

This suggests that the factors secreted by the fibroblasts have little effect on the growth of keratinocytes.

The results in the longliving FDM did show profound differences between the effects of reticular or papillary fibroblasts on the epidermis. First, the migration of keratinocytes is decreased on reticular equivalents. Second, in HSE-PF keratinocytes can maintain their proliferative capacity for longer than in HSE-RF. After 10 weeks of air-exposed culture, HSE-PF contained around 3-4 viable (epidermal) cell layers, while HSE-RF contained around 1-2 viable cell layers.

Example 5

Figure 2:
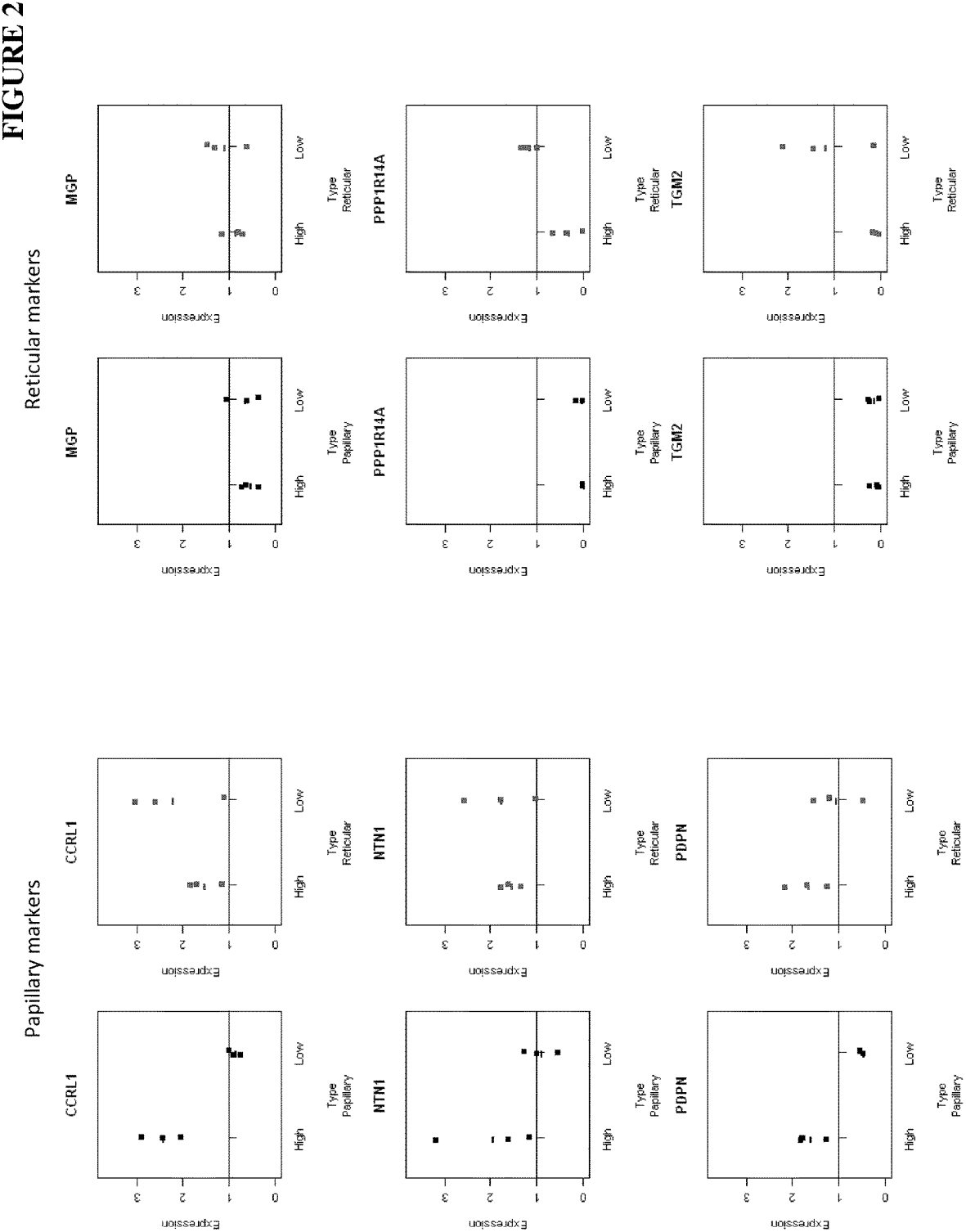
FIG. 2 shows the results of qPCR for marker genes in papillary and reticular fibroblast treated with verbascoside.

Compound Screening According to their Activity Towards Papillary and Reticular Fibroblasts Material and Methods
Cell Culture
The fibroblasts were isolated and cultured as described above (example 1).
Screening of Compounds
12000 reticular or papillary fibroblasts were seeded in 12 well culture plates (Costar). The fibroblasts were cultured for 5 days until 90% of the surface area was covered. Two different concentrations (low/high) of compounds were applied for 24 hrs. Pictures were taken before and after application. No differences in morphology and were observed (data not shown). RNA was isolated as described in example 1.
qPCR Analysis
qPCR analysis was performed using 3 papillary (CCRL1, NTN1 and PDPN) and 3 reticular (MGP, PPP1R14A and TGM2) markers, according to example 1. The expression was normalized using two reference genes (SND1 and EI24). The effect of verbascoside was determined by comparing the expression of the genes to the expression of vehicle treated fibroblasts.
Results of qPCR Analysis
One compound (Verbascoside, concentrations tested: high=0.01% v/v, low=0.0001% v/v) was able to alter the reticular signature into a papillary signature. The results of the screening are shown in FIG. 2.

REFERENCES

1. Sorrell J M, Caplan A I. Fibroblasts-a diverse population at the center of it all. *Int Rev Cell Mol Biol* 2009; 276: 161-214. Ref Type: Journal
2. Kalluri R, Zeisberg M. Fibroblasts in cancer. *Nat Rev Cancer* 2006; 6: 392-401. Ref Type: Journal
3. Maier A B, Westendorp R G. Relation between replicative senescence of human fibroblasts and life history characteristics. *Ageing Res Rev* 2009; 8: 237-243. Ref Type: Journal
4. Schonherr E, Beavan L A, Hausser H, Kresse H, Culp L A. Differences in decorin expression by papillary and reticular fibroblasts in vivo and in vitro. *Biochem J* 1993; 290 (Pt 3): 893-899. Ref Type: Journal
5. Sorrell J M, Caplan A I. Fibroblast heterogeneity: more than skin deep. *J Cell Sci* 2004; 117: 667-675. Ref Type: Journal
6. Azzarone B, ieira-Coelho A. Heterogeneity of the kinetics of proliferation within human skin fibroblastic cell populations. *J Cell Sci* 1982; 57: 177-187. Ref Type: Journal
7. Harper R A, Grove G. Human skin fibroblasts derived from papillary and reticular dermis: differences in growth potential in vitro. *Science* 1979; 204: 526-527. Ref Type: Journal
8. Izumi T, Tajima S, Nishikawa T. Differential expression of alpha 1 and alpha 2 chains of type VI collagen in the upper, middle, and lower dermal fibroblasts in vitro. *J Biochem* 1995; 117: 1004-1007. Ref Type: Journal
9. Tajima S, Pinnell S R. Collagen synthesis by human skin fibroblasts in culture: studies of fibroblasts explanted from papillary and reticular dermis. *J Invest Dermatol* 1981; 77: 410-412. Ref Type: Journal
10. Feldman S R, Trojanowska M, Smith E A, Leroy E C. Differential responses of human papillary and reticular fibroblasts to growth factors. *Am J Med Sci* 1993; 305: 203-207. Ref Type: Journal
11. Tajima S, Izumi T. Differential in vitro responses of elastin expression to basic fibroblast growth factor and transforming growth factor beta 1 in upper, middle and lower dermal fibroblasts. *Arch Dermatol Res* 1996; 288: 753-756. Ref Type: Journal
12. Mine S, Fortunel N O, Pageon H, Asselineau D. Aging alters functionally human dermal papillary fibroblasts but not reticular fibroblasts: a new view of skin morphogenesis and aging. *PLoS ONE* 2008; 3: e4066. Ref Type: Journal
13. Sorrell J M, Baber M A, Caplan A I. Site-matched papillary and reticular human dermal fibroblasts differ in their release of specific growth factors/cytokines and in their interaction with keratinocytes. *J Cell Physiol* 2004; 200: 134-145. Ref Type: Journal
14. Gilchrest B A, Krutmann J. Skin Aging. Springer Berlin Heidelberg, 2006. Ref Type: Book, Whole
15. Makrantonaki E, Zouboulis C C. Molecular mechanisms of skin aging: state of the art. *Ann N Y Acad Sci* 2007; 1119: 40-50. Ref Type: Journal
16. Du P, Kibbe W A, Lin S M. lumi: a pipeline for processing Illumina microarray. *Bioinformatics* 2008; 24: 1547-1548. Ref Type: Journal
17. Smyth G K. Linear models and empirical bayes methods for assessing differential expression in microarray experiments. *Stat Appl Genet Mol Biol* 2004; 3: Article3. Ref Type: Journal
18. Benjamini Y, Hochberg Y. Controlling the False Discovery Rate—A Practical and Powerful Approach to Multiple Testing. *Journal of the Royal Statistical Society Series B-Methodological* 1995; 57: 289-300. Ref Type: Journal
19. Dennis G, Jr., Sherman B T, Hosack D A, Yang J, Gao W, Lane H C, Lempicki R A. DAVID: Database for Annotation, Visualization, and Integrated Discovery. *Genome Biol* 2003; 4: 3. Ref Type: Journal
20. Vandesompele J, De P K, Pattyn F, Poppe B, Van R N, De P A, Speleman F. Accurate normalization of real-time quantitative RT-PCR data by geometric averaging of multiple internal control genes. *Genome Biol* 2002; 3: RESEARCH0034. Ref Type: Journal
21. Sorrell J M, Baber M A, Caplan A I. Clonal characterization of fibroblasts in the superficial layer of the adult human dermis. *Cell Tissue Res* 2007; 327: 499-510. Ref Type: Journal
22. Freedman B M, Rueda-Pedraza E, Waddell S P. The epidermal and dermal changes associated with microdermabrasion. *Dermatol Surg* 2001; 27: 1031-1033. Ref Type: Journal

The invention claimed is:

1. In vitro method for screening for compounds that activate PDPN gene expression in papillary fibroblasts, the method comprising the following steps:

(a) preparing a first and a second sample of papillary fibroblasts in vitro;

(b) bringing a compound into contact with the first sample of papillary fibroblasts, and leaving the second sample of papillary fibroblasts untreated, wherein the compound is a botanical extract;

(c) measuring the expression of a single gene consisting of the PDPN gene in said first and second samples of papillary fibroblasts, by performing PCR with primers of SEQ ID NO: 9 and SEQ ID NO: 10; and (d) selecting the compound for possible incorporation into a cosmetic composition when an activation of at least 1.5 fold of the expression of said PDPN gene is measured in the first sample of papillary fibroblasts compared with the second sample of papillary fibroblasts.

* * * * *